(12) United States Patent
Weber et al.

(10) Patent No.: US 9,968,342 B2
(45) Date of Patent: May 15, 2018

(54) HANDLE FOR SURGICAL INSTRUMENTS

(71) Applicant: Arthrex, Inc.

(72) Inventors: Robert M. Weber, Chino Hills, CA (US); Philip S. O'Quinn, Naples, FL (US)

(73) Assignee: Arthrex, Inc., Naples, FL (US)

( * ) Notice: Subject to any disclaimer, the term of this patent is extended or adjusted under 35 U.S.C. 154(b) by 639 days.

(21) Appl. No.: 13/654,970

(22) Filed: Oct. 18, 2012

(65) Prior Publication Data

US 2013/0103007 A1  Apr. 25, 2013

Related U.S. Application Data

(63) Continuation of application No. 11/700,915, filed on Feb. 1, 2007, now Pat. No. 8,382,789.

(60) Provisional application No. 60/763,914, filed on Feb. 1, 2006.

(51) Int. Cl.
| A61B 17/00 | (2006.01) |
|---|---|
| A61B 17/29 | (2006.01) |
| A61B 17/16 | (2006.01) |
| A61B 17/28 | (2006.01) |

(52) U.S. Cl.
CPC .......... *A61B 17/00* (2013.01); *A61B 17/2909* (2013.01); *A61B 17/1604* (2013.01); *A61B 17/1608* (2013.01); *A61B 17/2833* (2013.01); *A61B 2017/2837* (2013.01); *A61B 2017/2923* (2013.01); *A61B 2017/2946* (2013.01)

(58) Field of Classification Search
CPC ................ A61B 17/00; A61B 17/2909; A61B 2017/2946; A61B 2017/2923; A61B 2017/2837; A61B 17/1608; A61B 17/2833

USPC ........ 606/205, 1, 51, 52; 600/104, 141, 142; 81/418, 176.3, 119
See application file for complete search history.

(56) References Cited

U.S. PATENT DOCUMENTS

| 4,813,414 A * | 3/1989 | Costagliola ........ A61B 17/2812 |
| | | 606/151 |
| 5,184,625 A | 2/1993 | Cottone, Jr. et al. |
| 5,496,347 A * | 3/1996 | Hashiguchi ............ A61B 17/29 |
| | | 600/564 |
| 5,609,601 A | 3/1997 | Kolesa et al. |
| 5,626,608 A | 5/1997 | Cuny et al. |
| 5,735,873 A | 4/1998 | MacLean |
| 6,071,299 A * | 6/2000 | Dingler et al. ................ 606/205 |
| 7,001,382 B2 | 2/2006 | Gallo, Sr. |

(Continued)

FOREIGN PATENT DOCUMENTS

| DE | 42 23 162 | 1/1994 |
| DE | 298 06 799 | 6/1998 |

(Continued)

*Primary Examiner* — Corrine McDermott
*Assistant Examiner* — Tin Nguyen
(74) *Attorney, Agent, or Firm* — Rubin and Rudman LLP

(57) ABSTRACT

A handle for surgical instruments that has a "wishbone" configuration. In one embodiment, the instrument is provided with a ratchet mechanism allows two operating handles to be locked in a predetermined position (for example, when the surgical instrument that is maneuvered is in use) or to move relative to each other when the ratchet is partially or fully released (for example, when the surgical instrument that is maneuvered is not in use). In another embodiment, the instrument is provided with a rotary gear mechanism.

5 Claims, 3 Drawing Sheets

(56) References Cited

U.S. PATENT DOCUMENTS

| | | | |
|---|---|---|---|
| 2002/0143346 A1* | 10/2002 | McGuckin et al. | 606/139 |
| 2003/0120290 A1* | 6/2003 | Danitz et al. | 606/151 |
| 2005/0080320 A1* | 4/2005 | Lee | A61B 17/02 |
| | | | 600/214 |

FOREIGN PATENT DOCUMENTS

| | | |
|---|---|---|
| DE | 103 14 072 | 10/2004 |
| DE | 103 53 605 | 6/2005 |
| EP | 0 134 251 | 3/1985 |
| FR | 2 566 261 | 12/1985 |
| GB | 702 683 | 1/1954 |
| WO | WO 81/03122 | 11/1981 |

* cited by examiner

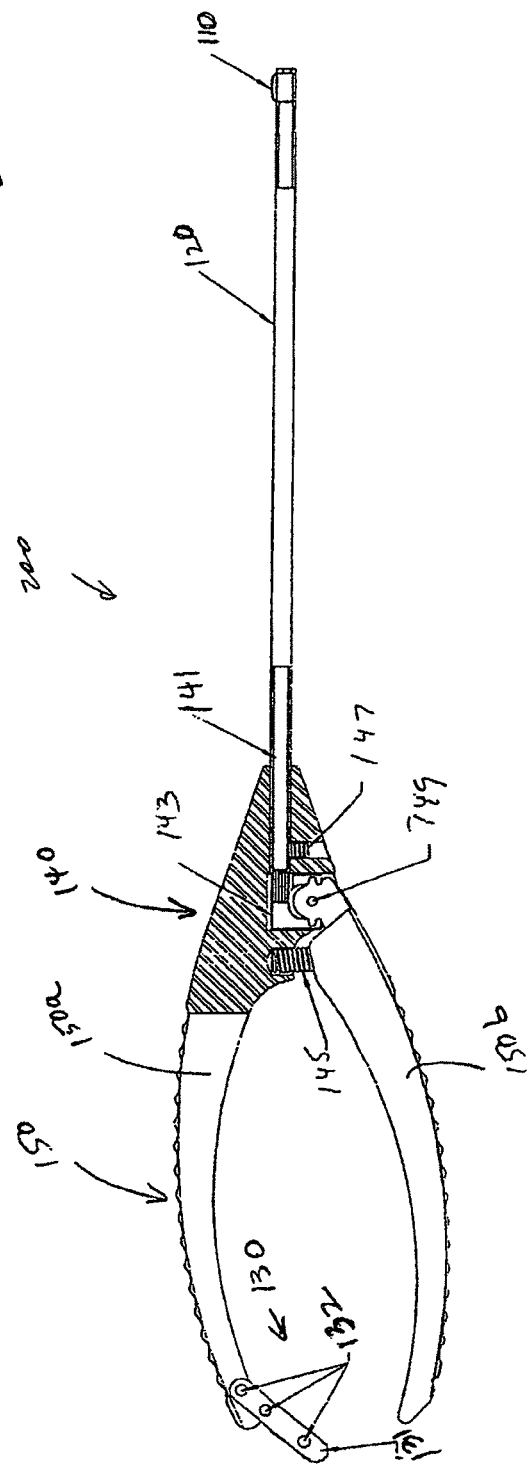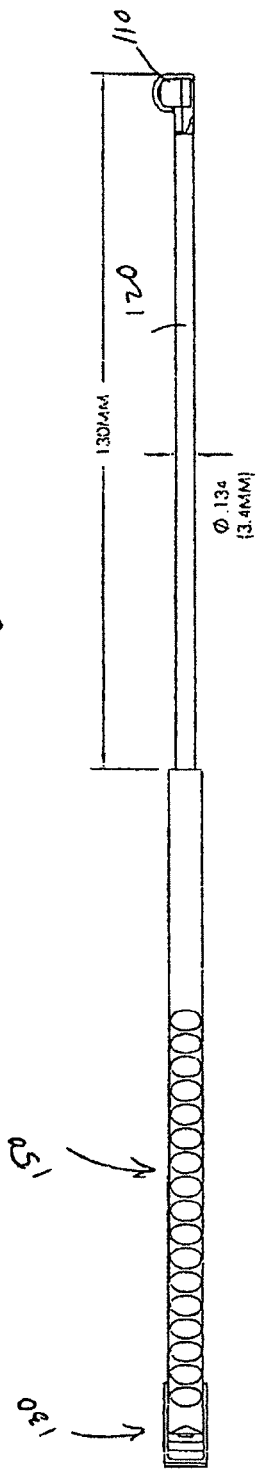

HANDLE FOR SURGICAL INSTRUMENTS

CROSS-REFERENCE TO RELATED APPLICATIONS

This is a continuation of application Ser. No. 11/700,915, filed Feb. 1, 2007, which claims the benefit of U.S. Provisional Application Ser. No. 60/763,914, filed on Feb. 1, 2006, the disclosures of which are hereby incorporated by reference in their entirety.

FIELD OF THE INVENTION

The present invention relates to the field of surgery and, in particular, to a novel instrument handle for aiding in manipulating anatomical tissue or suture during endoscopic surgical procedures.

BACKGROUND OF THE INVENTION

Endoscopic surgical procedures typically involve techniques and instruments that require access to a surgical work site that is within a patient's body. Access is normally provided through one or more portals formed directly in the patient's body or through one or more cannulas inserted into the patient's body through small incisions. A chosen surgical procedure is carried out by a surgeon through the use of elongated instruments inserted through these cannulas to reach and conduct various surgical procedures at the work site.

Since the work site is only accessible through a small portal or cannula, it is very difficult to manipulate tissue or tie sutures within the body. Because only a small incision is made during endoscopic surgery, it is also often difficult to grab small regions of tissue and to simultaneously or subsequently apply a desired tension on the tissue, either in a direction toward or away from the arthroscopic portal. Further, manipulation of anatomical tissue at the work site during endoscopic surgeries frequently requires simultaneous use of additional instruments that are needed during various surgical steps such as cutting or removing tissue, or suturing or tying knots.

Accordingly, a need exists for an improved handle for surgical instruments that allows controlled tissue manipulation and retraction, as well as controlled manipulation of suture or other material elements that are employed during or in conjunction with endoscopic surgeries. A need also exists for surgical instruments (such as graspers, punches or scissors, among others) that are stable during arthroscopy and maintain the lifting/retracting orientation desired by the surgeon, without accidental slipping or shifting and with minimal soft tissue edema to the patient. Surgical instruments with a handle having an improved design that allows a surgeon to grip the handle ergonomically and to effectively maneuver tissue or adjacent structures are also needed. Instruments with a simplified actuating mechanism which facilitates use of the instruments during surgery are further needed.

SUMMARY OF THE INVENTION

The present invention provides an improved handle for surgical instruments that has a "wishbone" handle configuration. In one embodiment, the handle is provided with a ratchet mechanism that allows two operating handles to be locked in a predetermined position (for example, when the surgical instrument that is maneuvered is in use) or to move relative to each other when the ratchet is partially or fully released (for example, when the surgical instrument that is maneuvered is not in use).

The ratchet may be actuated by an actuating mechanism that is located on the handle and that may include, for example, a mechanical thumb lever or trigger connected to the shaft of the instrument. The mechanical thumb lever or trigger is moveable between a first position when the ratchet is "locked" or "closed," an intermediary position when the ratchet is "partially-open," and a forward position when the ratchet is "fully-open" or "released." When the trigger is pushed down and/or moved forward, an end effect assembly of the instrument (for example jaws of a capsular punch or of a suture retriever) is maneuvered as desired. In this manner, the motion of the ratcheting mechanism including the mechanical thumb lever located on the instrument handle is translated through a connecting rod to urge the end effector assembly of the instrument into "open" or "closed" positions.

In another embodiment, the instrument is provided with a rotary gear mechanism for translating closure force on the handle into rotary motion of a shaft which, in turn, effects rotary motion at the distal (operating) end of the instrument.

Other features and advantages of the present invention will become apparent from the following description of the invention, which refers to the accompanying drawings.

BRIEF DESCRIPTION OF THE DRAWINGS

FIG. 6 illustrates a cross-sectional partial view of the instrument of FIG. 5; and FIG. 7 illustrates a top view of the instrument of FIG. 5.

DETAILED DESCRIPTION OF THE PREFERRED EMBODIMENTS

Figure 1:
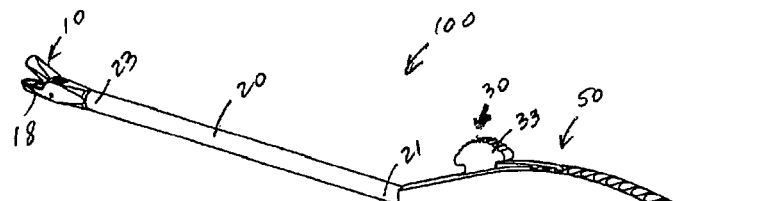
FIG. 1 illustrates a perspective view of an instrument having a handle according to a first embodiment of the present invention.

The present invention provides surgical instruments for endoscopic surgeries having an improved handle design, namely a "wishbone" configuration. The "wishbone" configuration of the handle allows a surgeon to grip the handle ergonomically and to effectively maneuver tissue or suture during surgery.

In one embodiment, the handle of the present invention is provided with a ratchet mechanism allows two operating handles having a "wishbone" configuration in a plier-type arrangement to be locked in a predetermined position (for example, when the surgical instrument is in use) or to move relative to each other when the ratchet is partially or fully released (for example, when the surgical instrument is not in use).

Referring to the drawings, where like elements are designated by like reference numerals, FIGS. 1-4 illustrate a first exemplary embodiment of a surgical instrument 100 provided with a handle 50 and ratchet mechanism 40 of the present invention. The surgical instrument 100 of FIGS. 1-4 may be employed in many surgical procedures, non-limiting examples including manipulating and retrieving suture, or grasping, punching or cutting tissue during surgery.

As illustrated in FIG. 1, the surgical instrument 100 includes handle 50, a shaft 20 having a proximal end 21 and a distal end 23, and an actuating mechanism 30 located on the handle and in communication with a ratchet mechanism 40. The actuating mechanism 30 is mechanically connected to the distal tip 23 and, when actuated, causes movement of the ratchet mechanism 40, which in turn actuates end effector assembly 10. In the exemplary embodiment shown in FIG. 1, the end effector assembly 10 comprises a pair of hinged jaws 18 that pivotably rotate between an open or closed position. However, the invention is not limited to this exemplary embodiment and the end effector assembly 10 may be part of any surgical instrument (for example, scissors, punches or graspers, among others) that requires manipulation through a handle, such as handle 50 of the present invention.

Figure 2:
FIG. 2 illustrates a partial view of the instrument of FIG. 1 with the ratchet in the "locked" position.
Figure 3:
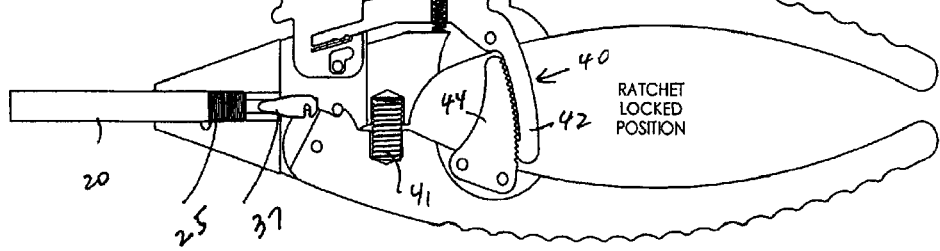
FIG. 3 illustrates a partial view of the instrument of FIG. 1 with the ratchet in the "partially-released" position.
Figure 4:
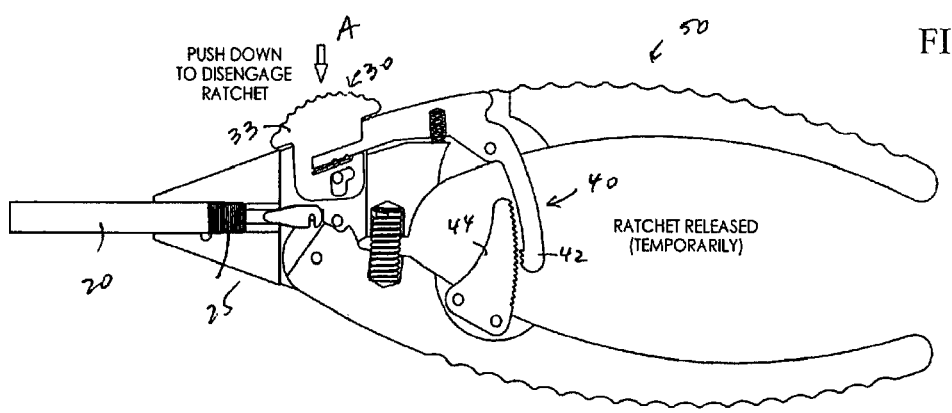
FIG. 4 illustrates a partial view of the instrument of FIG. 1 with the ratchet in the "fully-released" position.

FIGS. 2-4 illustrate in more detail the actuating mechanism 30 and the ratchet mechanism 40 which are part of handle 50 of the present invention. The actuating mechanism 30 comprises a mechanical lever or trigger 33 provided with a cam 37, a spring 25 and an inner rod or shaft (not shown). Shaft 20 of the instrument 100 houses the inner rod and is connected to the handle 50. Spring 25 is disposed between the proximal end of the inner rod and the proximal end of the shaft 20. Spring 25 forces the inner rod against the surface of cam 37. As explained below, trigger 33 is movable by a flexion or extension of a single digit between a forward position and a back position. When the trigger is moved forward, spring 25 urges inner rod distally and thus closes the jaws 18 of the instrument.

The ratchet mechanism 40 is actuated by mechanism 30 located on the handle 50 by the mechanical thumb lever or trigger 33 which is connected through a set of screws 41, 43 to the handle of the instrument. As shown in FIGS. 2-4, ratchet mechanism 40 comprises a first member 42 in communication with a second member 44. In the "locked" position illustrated in FIG. 2, first member 42 and second member 44 are completely locked to allow jaws 18 of the end effector assembly 10 to be in a "fully-open" position (FIGS. 1 and 2). To achieve this position, surface of cam 37 is designed such that the inner rod moves toward the proximal end of the instrument 100, whereby spring 25 causes the hinged jaws 18 to rotate to the "fully-open" position.

Pushing down on the mechanical thumb lever 33 of the actuating mechanism 30 in the direction of arrow "A" (FIG. 3) disengages the first member 42 from the second member 44 and allows the ratchet mechanism to be at an "intermediary" or "partially released" position. With the mechanical thumb lever of the actuating mechanism 30 in the "down" position, the user can then slide forward the mechanical thumb lever 33 in a forward, horizontal direction illustrated by arrow "B" in FIG. 4. In this manner, the first member 42 completely disengages the second member 44 and allows the ratchet mechanism to be in a "fully-released" or "fully-open" position. In turn, jaws 18 of the end effector assembly 10 are pivoted in a "closed" position to facilitate, for example, insertion of the instrument through tissue or to allow manipulation of additional instrumentation at the work site.

In use, the handle 50 of the instrument is held across the palm of a user's hand in a manner similar to a pair of pliers. Advantageously, the instrument can be held in the user's palm with the distal tip pointing away from the body, or reversed in the palm with distal tip pointing toward the body, affording the user greater flexibility in certain surgical situations. The user can grip the handle and trigger in one hand without the need for a finger ring or a thumb ring on the handle of the instrument. The actuating mechanism is positioned for easy manipulation by the user's thumb simply by pushing down followed by flexion or extension.

Figure 5:
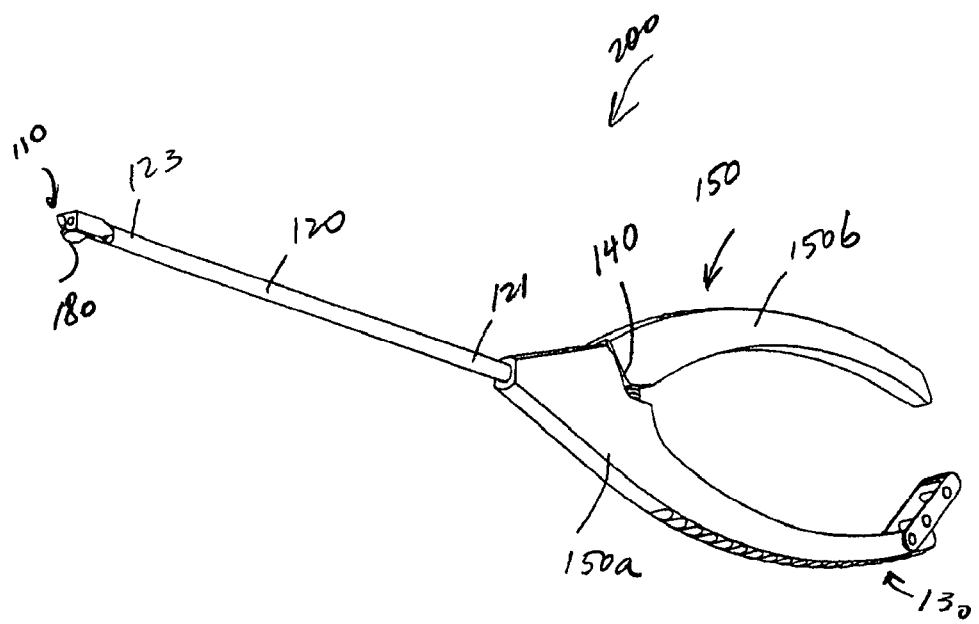
FIG. 5 illustrates a perspective view of an instrument having a handle according to a second embodiment of the present invention with a rotary gear mechanism.

FIGS. 5-7 illustrate another exemplary embodiment of a surgical instrument 200 provided with a handle 150 in a "wishbone configuration" and a rotary gear mechanism 140 (a rack and pinion gear mechanism) for translating the motion of closing and opening the handle into a rotary motion. As with the previously-described surgical instrument 100 illustrated with reference to FIGS. 1-4 above, the surgical instrument 200 of FIGS. 5-7 may be employed in many surgical procedures, non-limiting examples including punching or cutting tissue during surgery, grasping, or manipulating and retrieving suture, among many others.

The surgical instrument 200 includes handle 150, a shaft 120 having a proximal end 121 and a distal end 123, and in communication with a rotary gear mechanism 140. As shown in FIGS. 5 and 6, handle 150 includes two operating fingers, a stationary finger 150a (or stationary handle 150a) and a movable finger 150b (or movable handle 150b). When the movable finger 150b is actuated, by exerting compressive pressure upon it, for example, the movable finger 150b causes movement of the rotary gear mechanism 140, which in turn actuates rotation of end effector assembly 110.

In the exemplary embodiment shown in FIG. 5, the end effector assembly 110 comprises a rotary punch 180 that pivotably rotates between an open or closed position. However, the invention is not limited to this exemplary embodiment and the end effector assembly 110 may be part of any surgical instrument (for example, scissors, punches or graspers, among others) that requires rotary manipulation through a handle, such as handle 150 of the present invention.

As illustrated in FIGS. 5 and 6, handle 150 is also provided with a locking mechanism 131 provided with locking pins 132. Locking mechanism 131 may engage and subsequently lock the two operating fingers 150a, 150b when movable finger 150b is actuated.

FIGS. 6 and 7 illustrate in more detail the rotary gear mechanism 140 which is part of handle 150 of the present invention and is a rack and pinion mechanism. The rotary gear mechanism 140 comprises a rotary gear shaft 141 (which is housed by shaft 120 of the instrument 200 and is connected to the handle 150), rotary rack 143, wishbone spring 145, reverse punch set screw 147 and handle pin 149.

The above description and drawings illustrate preferred embodiments which achieve the objects, features and advantages of the present invention. Accordingly, it is not intended that the present invention be limited to the illustrated embodiments, but only by the appended claims.

What is claimed is:

1. A surgical instrument, comprising:
a shaft;
a rotary end effector assembly disposed at a most distal end of the shaft;
a handle extending from the shaft, the handle having a wishbone configuration, wherein the handle includes a movable handle and a stationary handle, the stationary handle extending away from the shaft, the stationary handle being provided with a locking mechanism provided on the stationary handle and attached to the stationary handle, the locking mechanism being provided with locking pins, the locking mechanism engaging and subsequently locking the movable handle and the stationary handle when the movable handle is actuated, the movable handle extending away from the shaft and communicating with a rotary gear mechanism, the movable handle and the stationary handle being provided substantially symmetric relative to a longitudinal axis of the instrument; and a rod extending along the shaft and linking the rotary end effector assembly at the most distal end of the shaft to the rotary gear mechanism, wherein the rotary gear mechanism includes a rotary rack and a wishbone pin, wherein the rotary gear mechanism translates closure force on the movable handle into rotary motion of the shaft, which in turn effects rotary motion of the rotary end effector assembly at the most distal end of the shaft, wherein, when the movable handle is actuated by exerting compressive pressure upon it, the movable handle causes movement of the rotary gear mechanism which in turn actuates rotation of the rotary end effector assembly.

2. The surgical instrument of claim 1, wherein the instrument is an arthroscopic instrument.

3. The surgical instrument of claim 1, wherein the movable handle and the stationary handle are adapted to be gripped without the need for finger or thumb rings.

4. The surgical instrument of claim 1, wherein the rotary end effector assembly comprises a rotary punch.

5. The surgical instrument of claim 1, wherein the rotary end effector assembly requires rotary manipulation through the handle.

* * * * *